(12) United States Patent
Wright

(10) Patent No.: US 7,417,733 B2
(45) Date of Patent: Aug. 26, 2008

(54) CHAMBER PARTICLE DETECTION SYSTEM

(75) Inventor: Mark Wright, Meridian, ID (US)

(73) Assignee: Lam Research Corporation, Fremont, CA (US)

( * ) Notice: Subject to any disclaimer, the term of this patent is extended or adjusted under 35 U.S.C. 154(b) by 236 days.

(21) Appl. No.: 11/350,999

(22) Filed: Feb. 8, 2006

(65) Prior Publication Data

US 2007/0182963 A1  Aug. 9, 2007

(51) Int. Cl.
*G01N 21/00* (2006.01)

(52) U.S. Cl. ........................ 356/337; 356/336

(58) Field of Classification Search ......... 356/335–343, 356/237.1–237, 23.72, 432–448; 219/121.41; 702/24; 250/559.04, 559.24
See application file for complete search history.

(56) References Cited

U.S. PATENT DOCUMENTS

| | | | | |
|---|---|---|---|---|
| 5,255,089 A * | 10/1993 | Dybas et al. | ................. | 348/126 |
| 5,372,673 A * | 12/1994 | Stager et al. | ................... | 438/8 |
| 5,467,188 A * | 11/1995 | Miyashita | ................... | 356/336 |
| 5,691,812 A * | 11/1997 | Bates et al. | .............. | 356/243.4 |
| 5,909,276 A * | 6/1999 | Kinney et al. | ............ | 356/237.2 |
| 5,940,175 A * | 8/1999 | Sun | .......................... | 356/237.3 |
| 5,943,130 A | 8/1999 | Bonin et al. | | |
| 5,997,642 A * | 12/1999 | Solayappan et al. | ........... | 118/50 |
| 6,015,718 A * | 1/2000 | Rathbone | ..................... | 438/17 |
| 6,392,745 B1 * | 5/2002 | Mavliev et al. | ............... | 356/37 |
| 6,490,530 B1 * | 12/2002 | Wyatt | .......................... | 702/24 |
| 6,825,437 B2 * | 11/2004 | Nakano et al. | ......... | 219/121.41 |
| 6,941,791 B1 * | 9/2005 | Sanders et al. | ................. | 72/458 |
| 2002/0148824 A1 | 10/2002 | Hauf et al. | | |
| 2003/0076494 A1 | 4/2003 | Bonin et al. | | |
| 2003/0140988 A1 | 7/2003 | Gandikota et al. | | |

FOREIGN PATENT DOCUMENTS

WO  WO 2005/091970  10/2005

OTHER PUBLICATIONS

International Search Report (3 pages).

* cited by examiner

*Primary Examiner*—Sang Nguyen
(74) *Attorney, Agent, or Firm*—Martine Penilla & Gencarella, LLP

(57) ABSTRACT

Broadly speaking, the embodiments of the present invention fill the need by providing an improved chamber particle source identification mechanism. The in-situ chamber particle source identification method and apparatus can greatly shorten the time it takes to identify chamber particle source, which could improve the chamber throughput for production system. The method and apparatus can also be used to test components for particle performance during chamber engineering development stage. In one embodiment, an in-situ chamber particle monitor assembly for a semiconductor processing chamber includes at least one laser light source. The at least one laser light source can scan laser light in a chamber process volume within the processing chamber. The in-situ chamber particle monitor assembly also includes at least one laser light collector. The at least one laser light collector can collect laser light emitted from the at least one laser light source. The chamber particle monitor assembly also includes an analyzer external to the processing chamber that analyzes signals representing the laser light collected by the at least one laser light collector to provide chamber particle information.

19 Claims, 5 Drawing Sheets

CHAMBER PARTICLE DETECTION SYSTEM

BACKGROUND

Particle performance is of concern in processing semiconductor substrates such as silicon wafers due to reduction in yield caused by particles adhered to the surface of such substrates. Particles in the process chamber that fall on the substrate surface during or after substrate processing can reduce yield. Therefore, it is critical to control particle counts in the process chamber to the minimum to ensure good yield.

Particles in the process chamber can come from many sources. Process gases and substrate processing can generate particles. Films, either from process gases or from process byproducts, deposited on the components in the process chamber or on chamber wall(s) can also generate particles. Particles can also be introduced into the process chamber during chamber hardware maintenance by various mechanisms, such as cleaning solution residues remaining in the chamber when placing the component back into chamber. The O-ring on the chamber gate valve can also generate particles if the gate valve is clamped too tight or if the O-ring is of poor quality.

Traditionally, particle performance of a process chamber is monitored by measuring particle size and number (or count) on a substrate after the substrate is processed. The particle performance measurement can be done regularly to monitor the chamber performance or can be done after chamber hardware maintenance to qualify the process chamber. If a high particle count on the substrate is detected, the particle source (s) needs to be identified and the problem(s) needs to be solved before further substrate processing can be continued or before the chamber can be qualified.

Traditionally, particle source identification is done by running design of experiment (DOE) of various chamber processing and/or hardware parameters. Substrates processed with the DOE are measured for particle performance to determine which parameter(s) affects the particle size and counts. However, such a particle source identifying process is very labor and time intensive.

In view of the foregoing, there is a need for a method and apparatus that provides an improved chamber particle source identification mechanism to reduce the time and resources used to identify the particle source(s). The improved chamber particle source identification mechanism can improve overall chamber particle performance and throughput performance.

SUMMARY

Broadly speaking, the embodiments of the present invention fill the need by providing an improved chamber particle source identification mechanism. The in-situ chamber particle source identification method and apparatus can greatly shorten the time it takes to identify chamber particle source, which could improve the chamber throughput for production system. The method and apparatus can also be used to test components for particle performance during chamber engineering development stage. It should be appreciated that the present invention can be implemented in numerous ways, including as a process, an apparatus, or a system. Several inventive embodiments of the present invention are described below.

In one embodiment, an in-situ chamber particle monitor assembly for a semiconductor processing chamber includes at least one laser light source. The at least one laser light source can scan laser light in a chamber process volume within the processing chamber. The in-situ chamber particle monitor assembly also includes at least one laser light collector. The at least one laser light collector can collect laser light emitted from the at least one laser light source. The chamber particle monitor assembly also includes an analyzer external to the processing chamber that analyzes signals representing the laser light collected by the at least one laser light collector to provide chamber particle information.

In another embodiment, a process chamber with an in-situ chamber particle monitor assembly to identify chamber particle source includes a substrate support within the process chamber. The process chamber also includes a chamber top plate disposed over the substrate support. In addition, the process chamber includes at least one laser light source, wherein the at least one laser light source can scan laser light in a chamber process volume within the process chamber and the chamber process volume is defined between the substrate support and the chamber top plate. The process chamber also includes at least one laser light collector, wherein the at least one laser light collector can collect laser light emitted from at least one laser light source. Additionally, the process chamber includes an analyzer external to the processing chamber that analyzes signals representing the laser light collected by the at least one laser light collect to provide chamber particle information.

In yet another embodiment, a method of collecting chamber particle information in-situ includes scanning laser light emitted from a laser light source in a process volume inside a process chamber. The method also includes collecting the laser light in the process chamber by multiple laser light collectors. In addition, the method includes analyzing the collected laser light to determine chamber particle information.

Other aspects and advantages of the invention will become apparent from the following detailed description, taken in conjunction with the accompanying drawings, illustrating by way of example the principles of the invention.

BRIEF DESCRIPTION OF THE DRAWINGS

The present invention will be readily understood by the following detailed description in conjunction with the accompanying drawings, and like reference numerals designate like structural elements.

DETAILED DESCRIPTION OF THE EXEMPLARY EMBODIMENTS

Figure 1A:
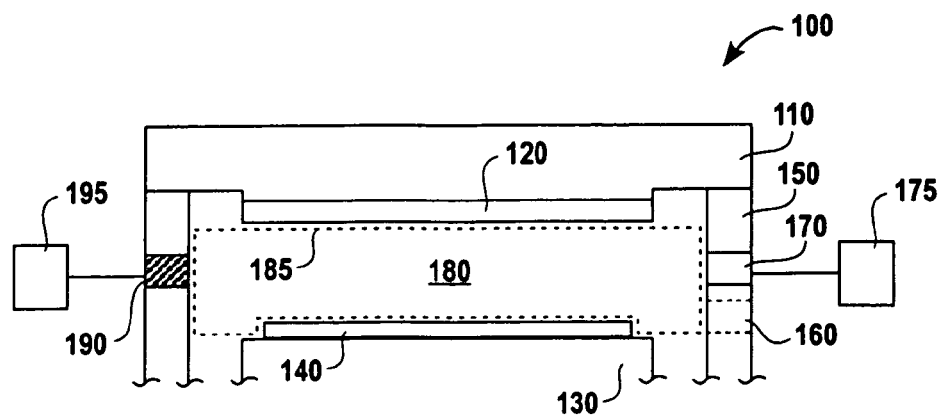
FIG. 1A shows a schematic cross-sectional diagram of one embodiment of an in-situ particle detection system in a process chamber.

Several exemplary embodiments for an improved and more effective chamber particle identification system, method and apparatus will now be described. It will be apparent to those skilled in the art that the present invention may be practiced without some or all of the specific details set forth herein.

As described earlier, the traditionally particle source identification method of running design of experiment (DOE) of various chamber processing and/or hardware parameters is very time and resources consuming. Speedy particle source identification is very important in reducing the time it takes to bring the process chamber back into manufacturing state. An effective in-situ chamber particle identification method and apparatus can provide instant particle information in the process chamber. By reviewing the particle information, which could include particle sizes, numbers, and locations of the particles, particle sources can be revealed or directions for further study can be identified. For example, if the chamber particles are heavily located near the transfer port, the transfer port can be suspected to cause the particle problem. Components of the transfer port, such as an O-ring, can be examined or replaced to see if the particle problem would be resolved. In addition, the operating parameters of the transfer port can also be studied to test their effects on the particle problem. For example, the clamping force on the transfer port door can be reduced to test if the particle problem can be reduced, as clamping the transfer port door too hard can damage the O-ring to cause particle problem.

The direct and instant chamber particle information can greatly shorten the time it takes to identify chamber particle sources, which could improve the chamber throughput for the manufacturing system. In addition, the method and apparatus can also be used to test components for particle performance during a chamber engineering development stage to shorten the chamber development time.

One embodiment of the present invention scans laser light by at least one laser light source into a process volume in the process chamber. In one embodiment, the process volume is the region above and around the substrate support in the process chamber and below the chamber top plate. The process chamber can be any type of process chamber, such as chemical vapor deposition chamber, plasma etching chamber, or thermal vapor deposition chamber, as long as the chamber is enclosed. The particles in the region covered (or scanned) by the laser light source(s) would reflect the laser light and affect the laser light pattern in the region studied. A laser is the preferred light source because its light is a single wavelength (and therefore it is one color—typically red or infrared for particle counters). Solid state laser diodes can be used in one embodiment because of their small size, light weight, and mean time between failures (MTBF).

The laser light can be picked up by at least one laser light detector, such as a photodetector or a camera, installed in the chamber. A photodetector is an electric device that is sensitive to light. Any light that strikes the photodetector causes the photodetector to emit an electric pulse. The electrical pulses can be analyzed to be correlated to particle number, sizes and locations. Digital cameras can also be used due to their sensitivity to light. The light detector can continuously collect particle data to monitor the chamber particle performance or can collect particle data only during trouble-shooting.

FIG. 1A shows a cross-sectional view of an embodiment of a process chamber 100 that has a chamber top plate 110, which includes a gas distribution plate (or shower head) 120. In one embodiment, the gas distribution plate 120 can also be a top electrode for a plasma processing chamber. Chamber 100 also has a substrate support 130 that can support a substrate 140. Chamber wall(s) 150 has a substrate transfer port 160 that allows substrate 140 to be transferred in and out of the process chamber 100. Chamber wall 150 could be one piece or multiple pieces (walls). Laser light source 170 is installed within the chamber wall 150. Laser light source 170 is controlled by a controller 175 that control its scanning frequency and direction. In one embodiment, the laser light source 170 scans across the region 180 above and around the substrate support 140 130. Region 180 is illustrated by the dotted line 185 and corresponds to the chamber process volume. The substrate 140 can be present or not present during the particle source identification process. The laser light is collected by light collector 190 that is placed on the chamber wall 150. Since the particles in the process chamber would reflect laser light and affect the laser light pattern, the locations and numbers of the particle in the process chamber can be captured by the laser light collector 190. The laser light collector 190 is connected to an analyzer 195 to analyze the signals (or pulses) collected.

The analyzed pulses can be correlated to particle counts, sizes and locations of the particles in the chamber. If there is only one light collector 190 in the process chamber, the particle images collected from the chamber would be two-dimensional (2-D). From the particle images collected, one can tell the particle counts, particle sizes and in what directions relative to the light collector 190 the particles are located. In order to get a three-dimensional (3-D) construction of images of particles in the process chamber, a plurality of light collectors 190 are needed. The plurality of light collectors 190 should be placed such that none of the light collectors share a common axis.

Figure 1B:
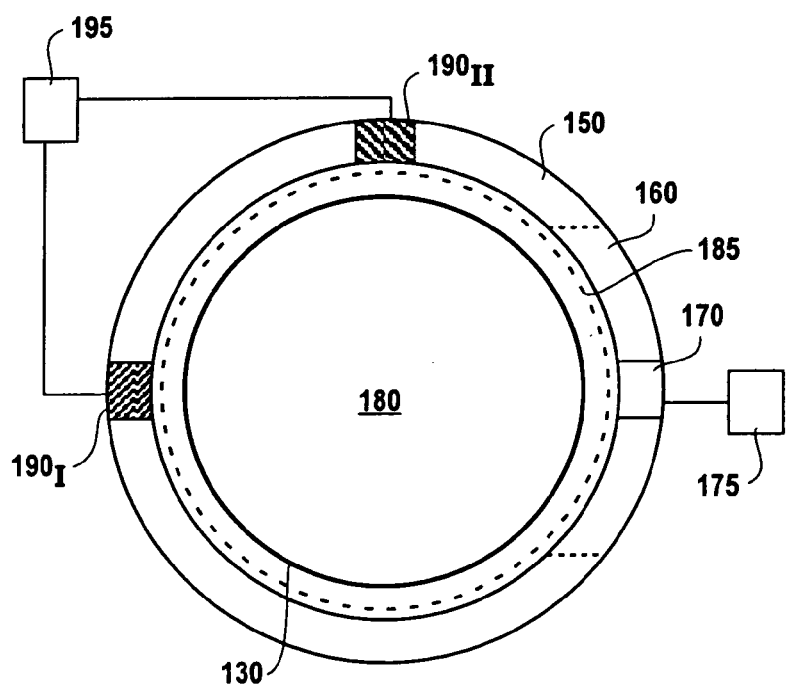
FIG. 1B shows an embodiment of a top view of the in-situ particle detection system in the process chamber of FIG. 1A.

FIG. 1B shows an embodiment of a top cross-sectional view of chamber 100 of FIG. 1A with one laser light source 170 and two laser light collectors $190_I$ and $190_{II}$. The laser light source 170 scans across the entire chamber process region 180, whose boundary is illustrated by dotted line 185. The two laser light collectors $190_I$ and $190_{II}$ collect laser light emitted from the laser light source 170. The number of particles, size of particles and locations of particle in the process chamber region 180 would affect the number and locations of laser light being reflected. Therefore, the laser light collected by the two light collectors 190 can be analyzed by the analyzer 195 to describe the number, the sizes and 3-D locations of the particles in the process chamber 100.

Figure 1C:
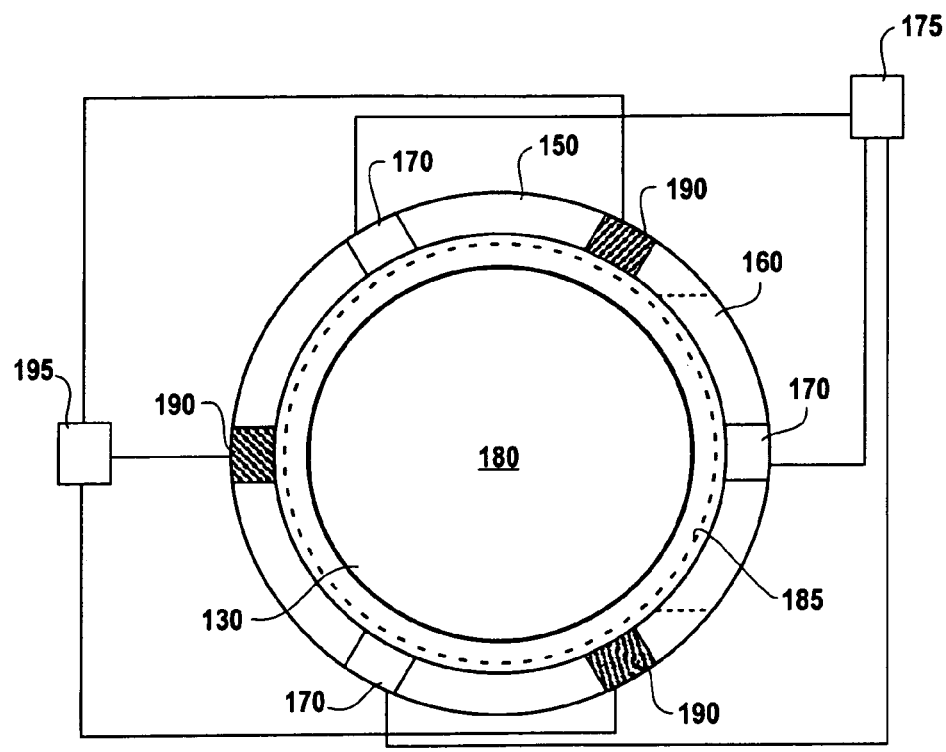
FIG. 1C shows another embodiment of a top view of the in-situ particle detection system in the process chamber of FIG. 1A.

In one embodiment, there could be more than one laser light source to ensure better coverage of laser light scanning across the chamber 100. FIG. 1C shows an embodiment of a process chamber 100 with 3 laser light sources 170 and 3 laser light collectors 190. One skilled in the art will appreciate that other combinations of number of laser light sources and laser light collectors are possible.

In addition to mounting the laser light source(s) and laser light collector(s) on the chamber wall, the laser light source(s) and the laser light collector(s) can also be mounted on a chamber liner. In some process systems, such as a plasma etch system, the chamber liner(s) is used to reduce film build-up on the chamber wall. Chamber liner could be made of one piece material, or made of multiple pieces (liners). Details of how a chamber liner is installed in a plasma etch chamber is described in U.S. Pat. No. 6,277,237, owned by the Assignee.

Figure 2A:
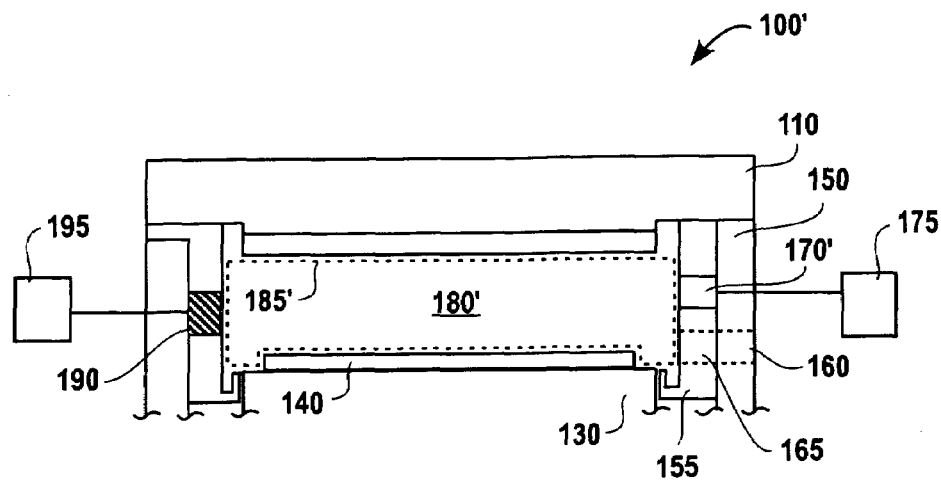
FIG. 2A shows a schematic cross-sectional diagram of one embodiment of an in-situ particle detection system in a process chamber with a chamber liner.

FIG. 2A shows a process chamber 100' that is similar to the chamber 100 of FIG. 1A. Chamber 100' has a chamber liner 155. At least one laser light source 170 and at least one laser light collector 190 are installed on the liner 155. The laser light source(s) 170 scan across the chamber process region 180', which is slightly smaller than the process region 180 of FIG. 1A due to the insertion of the chamber liner 155. There is a substrate transfer port 165 on the liner 155 that matches with the transfer port 160 on the chamber wall. Since the liner is replaceable, the laser light source(s) and the laser light collector(s) can be placed into the chamber when there is a need to identify particle source. Once the particle problem is solved, the laser light source(s) 170 and laser light collector(s) 190 can be removed with chamber liner 155, and a new chamber liner 155' without the laser light source(s) 170 and the laser light collector(s) 190 can be placed into the chamber to continue the manufacturing process.

Figure 2B:
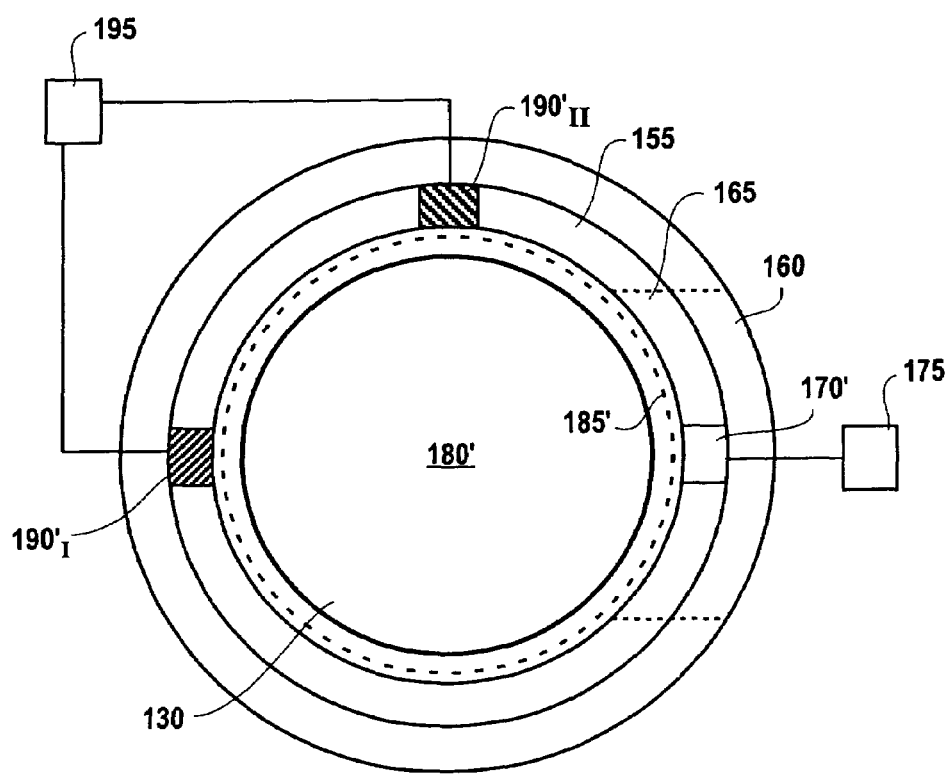
FIG. 2B shows an embodiment of a top view of the in-situ particle detection system in the process chamber of FIG. 2A.

FIG. 2B shows a top cross-sectional view of chamber 100' with one laser light source 170' and two laser light collectors $190_I'$ and $190_{II}'$, installed on the chamber liner 155. The two laser light collectors $190_I'$ and $190_{II}'$ enable the construction of 3-D images of particles in the process chamber 100 and allows the number, the sized, and 3-D locations of particles in the process region 180' in the chamber 100' to be determined. Similar to laser light source(s) and laser light collector(s) on the chamber wall, there could be more than one laser light source to ensure better coverage of laser light scanning across the chamber process region 180. Different combination of number of laser light sources and laser light collectors are possible.

Figure 3:
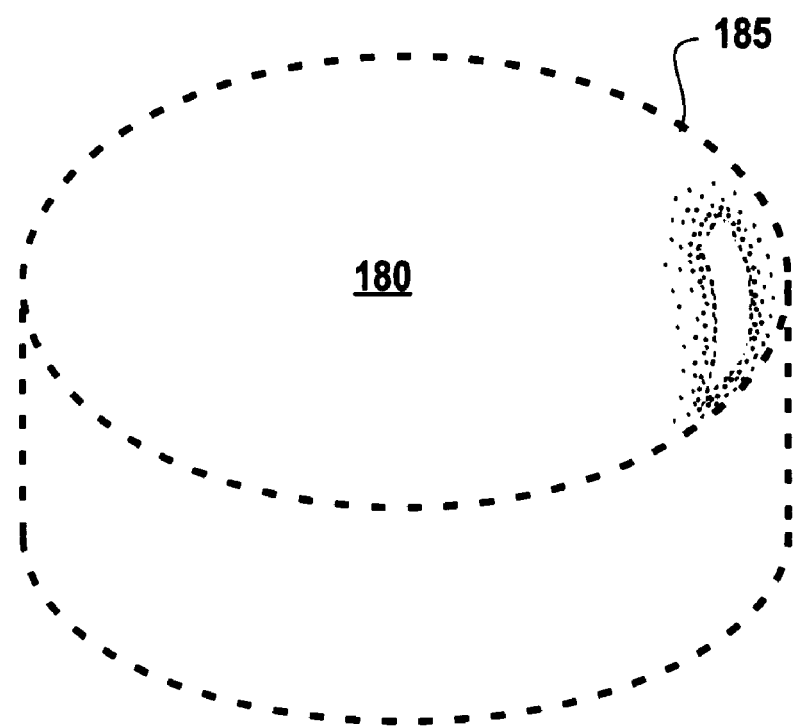
FIG. 3 shows a schematic diagram of a chamber volume studied by a particle detection system.

FIG. 3 shows an exemplary 3-D schematic drawing of region 180 surrounded by dotted boundary lines 185. The laser light pattern collected by the laser light collector(s) 190 of FIG. 2B shows a large amount of particles near the chamber transfer port 160. Based on the particle information illustrated in FIG. 3, further particle study on the transfer port 160 can be conducted. Additional analysis can lead to the conclusion that the transfer port O-ring releases large amounts of particles due to the transfer port door being clamped too tight and resulting in O-ring damage. By viewing the 3-D chamber particle images as a function of time, the origin and the movement of particles can also be traced. The 3-D images can be very useful in speeding up the chamber particle source identification.

Figure 4:
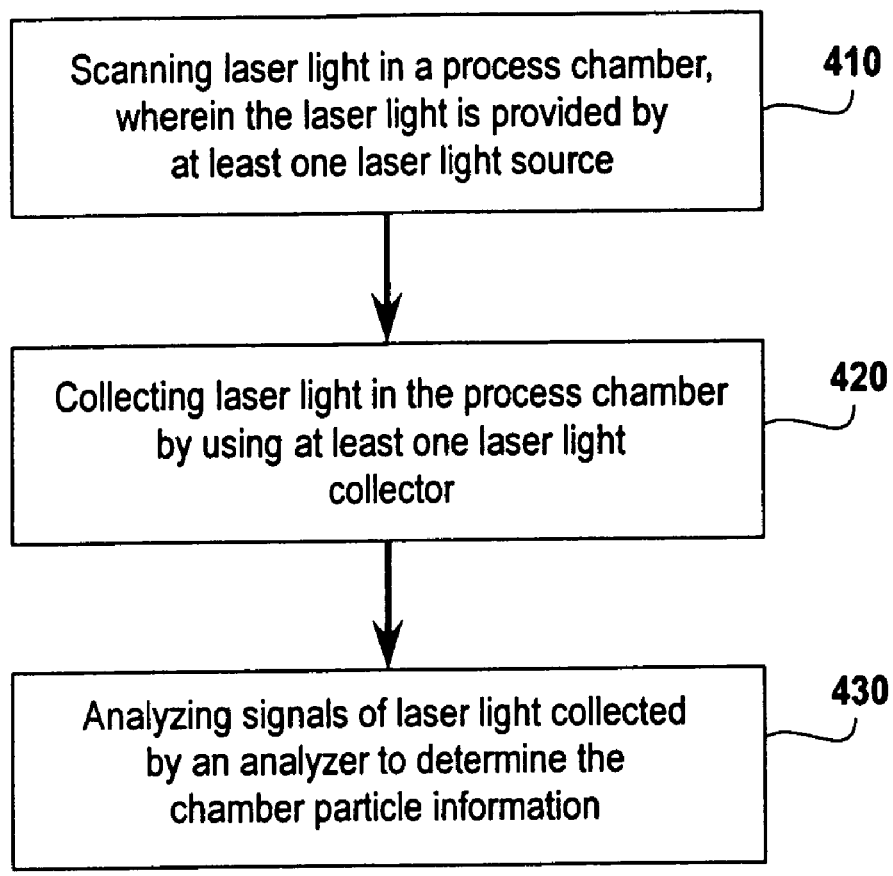
FIG. 4 shows a process flow of determining chamber particle information in a process chamber.

FIG. 4 shows a process flow of using the chamber particle detection system to detect particles in a process chamber. The process 400 starts at step 410 by scanning laser light in a process volume. In one embodiment, the process volume is defined between a chamber top plate and a substrate support, where the laser light is provided by one or more laser light sources. The process is then followed by collecting laser light in the process chamber from the process volume using at least one laser light collector at step 420. If three-dimensional chamber particle information is to be collected, there needs to be at least two laser light collectors. The at least two laser light collectors should be placed apart from each other and not directly opposite of each other. After the laser light is collected by the laser light collectors, the signals are analyzed by an analyzer to determine the chamber particle information at step 430.

The chamber particle information includes the particle counts, particle sizes, particle size distribution, and locations of the particles. By reviewing the pattern of particles distributed in the process chamber, the source(s) of particles can be revealed or direction of further study can be identified.

Although the foregoing invention has been described in some detail for purposes of clarity of understanding, it will be apparent that certain changes and modifications may be practiced within the scope of the appended claims. Accordingly, the present embodiments are to be considered as illustrative and not restrictive, and the invention is not to be limited to the details given herein, but may be modified within the scope and equivalents of the appended claims.

What is claimed is:

1. An in-situ chamber particle monitor assembly for a processing chamber, comprising:

at least one laser light source, wherein the at least one laser light source can scan laser light in a chamber process volume within the processing chamber;

a plurality of laser light collectors, wherein the plurality of laser light collectors can collect laser light emitted from the at least one laser light source, wherein the plurality of laser light collectors are placed in the processing chamber such that none of the plurality of laser light collectors share a common axis; and an analyzer external to the processing chamber that analyzes signals representing the laser light collected by the plurality of laser light collectors to provide chamber particle information, wherein the plurality of laser light collectors enables construction of three-dimensional (3-D) images of particle distribution within the processing volume.

2. The in-situ chamber particle monitor assembly of claim 1, wherein the chamber particle information comprises particle number, particle sizes and locations of particles.

3. The in-situ chamber particle monitor assembly of claim 1, wherein at least portions of both the at least one laser light source and the plurality of laser light collectors are embedded within a chamber wall.

4. The in-situ chamber particle monitor assembly of claim 1, wherein at least portions of both the at least one laser light source and the plurality of laser light collectors are embedded within a chamber liner.

5. The in-situ chamber particle monitor assembly of claim 1, wherein the chamber process volume encompasses a plane defined above a substrate support within the process chamber.

6. A process chamber with an in-situ chamber particle monitor assembly to identify chamber particle source, comprising:

a substrate support within the process chamber;

a chamber top plate disposed over the substrate support;

at least one laser light source, wherein the at least one laser light source can scan laser light in a chamber process volume within the process chamber and the chamber process volume is defined between the substrate support and the chamber top plate;

a plurality of laser light collectors, wherein the plurality of laser light collectors can collect laser light emitted from at least one laser light source, wherein the plurality of laser light collectors are placed in the processing chamber such that none of the plurality of laser light collectors share a common axis; and an analyzer external to the processing chamber that analyzes signals representing the laser light collected by the plurality of laser light collectors to provide chamber particle information, wherein the plurality of laser light collectors enables construction of three-dimensional (3-D) images of particle distribution within the processing volume.

7. The in-situ chamber particle monitor assembly of claim 6, wherein there are at least two laser light sources, the at least two laser light sources are placed apart from one another to provide light sources to the process chamber.

8. The process chamber of claim 6, wherein at least portions of both the at least one laser light source and the plurality of laser light collectors are embedded within a chamber wall.

9. The process chamber of claim 6, wherein a chamber wall is defined around the substrate support and a liner is disposed within the chamber wall.

10. The process chamber of claim 9, wherein at least portions of both the at least one laser light source and the plurality of laser light collectors are embedded within the chamber liner.

11. The process chamber of claim 10, wherein there are 3 laser light sources and 3 light source collectors.

12. The process chamber of claim 9, wherein there are a plurality of chamber liners and at least portions of both the at least one laser light source and the plurality of laser light collectors are embedded within the plurality of chamber liners.

13. A method of collecting chamber particle information in-situ, comprising:

scanning laser light emitted from a laser light source in a process volume inside a process chamber;

collecting the laser light in the process chamber by multiple laser light collectors, wherein the multiple laser light collectors are placed in the processing chamber such that none of the multiple laser light collectors share a common axis; and analyzing the collected laser light to determine chamber particle information wherein the multiple laser light collectors enables construction of three-dimensional (3-D) images of particle distribution within the processing volume.

14. The method of claim 13, wherein the process volume is defined between a chamber top plate and a substrate support.

15. The method of claim 13, further comprises:

embedding the laser light source and the multiple laser light collectors within a chamber wall.

16. The method of claim 13, further comprises embedding the laser light source and the multiple laser light collectors within a chamber liner.

17. The method of claim 16, wherein the chamber liner with the laser light source and multiple laser light collectors are removable.

18. The method of claim 13, wherein the chamber particle information includes particle size and distribution and particle location information within the process chamber.

19. The method of claim 13, wherein the 3-D image includes particle size information.

* * * * *